United States Patent
Benson et al.

(10) Patent No.: US 10,189,771 B2
(45) Date of Patent: Jan. 29, 2019

(54) ACRYLIC ADHESIVE COMPOSITION FROM PROTECTED PHOTOCROSSLINKING AGENTS

(71) Applicant: 3M INNOVATIVE PROPERTIES COMPANY, St. Paul, MN (US)

(72) Inventors: Karl E. Benson, St. Paul, MN (US); Ross E. Behling, Woodbury, MN (US); Anish Kurian, Woodbury, MN (US); Ryan B. Prince, St. Paul, MN (US); Joshua R. Wurst, North St. Paul, MN (US); Adam R. Wohl, Mahtomedi, MN (US); Robert J. Webb, Hudson, WI (US); Sehban Ozair, New Brighton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 110 days.

(21) Appl. No.: 15/550,830

(22) PCT Filed: Jan. 28, 2016

(86) PCT No.: PCT/US2016/015331
§ 371 (c)(1),
(2) Date: Aug. 14, 2017

(87) PCT Pub. No.: WO2016/133669
PCT Pub. Date: Aug. 25, 2016

(65) Prior Publication Data
US 2018/0029970 A1    Feb. 1, 2018

Related U.S. Application Data

(60) Provisional application No. 62/117,636, filed on Feb. 18, 2015.

(51) Int. Cl.
*C07C 69/54* (2006.01)
*C09J 133/08* (2006.01)
*C08F 220/18* (2006.01)

(52) U.S. Cl.
CPC ............ *C07C 69/54* (2013.01); *C08F 220/18* (2013.01); *C09J 133/08* (2013.01)

(58) Field of Classification Search
CPC ...... C07C 69/54; C09J 133/08; C08F 220/18; C08F 2/50
See application file for complete search history.

(56) References Cited

U.S. PATENT DOCUMENTS

| | | | |
|---|---|---|---|
| 4,304,705 A | 12/1981 | Heilmann |
| 4,619,979 A | 10/1986 | Kotnour |
| 4,777,276 A | 10/1988 | Rasmussen |
| 4,843,134 A | 6/1989 | Kotnour |
| 4,847,137 A | 7/1989 | Kellen |
| 5,505,279 A | 4/1996 | Louis |
| 5,637,646 A | 6/1997 | Ellis |
| 5,804,610 A | 9/1998 | Hamer |
| 6,235,922 B1 | 5/2001 | Robl |
| 7,838,110 B2 | 11/2010 | Zhu |
| 7,968,661 B2 | 6/2011 | Ellis |
| 2012/0329898 A1 | 12/2012 | Weikel |

FOREIGN PATENT DOCUMENTS

| | | |
|---|---|---|
| EP | 2733186 | 5/2014 |
| WO | WO 1996-007522 | 3/1996 |
| WO | WO 2012-091817 | 7/2012 |
| WO | WO 2012-148608 | 11/2012 |
| WO | WO 2015/019616 | 2/2015 |

OTHER PUBLICATIONS

Billmeyer, Textbook of Polymer Science, pp. 84-91 (1971).
Hubner, "Synthese and Reaktionen Von 2-Alkenyloxazolonen," Makromolekulare Chemie, 1970, vol. 11, No. 124, pp. 109-124.
Iwakura, "A Novel Preparation of Pseudoxazolones," Tetrahedron, 1967, vol. 23, pp. 3363-3373.
Kulkarni, "Effect of Asymmetric Centers on Free Radical Polymerization and the Properties of Polymers: Methacrylyl Alanine, Methacrylyl Glutamic Acid, Acrylyl Glutamic Acid, and Their Polymers," Journal of Polymer Science, Oct. 1961, vol. 54, No. 160, pp. 491-503.
Rauwendaal, Mixing in Polymer Processing, pp. 129, 176-177, and 185-186 (1991).
Taylor, "The Synthesis of Vinyl Peptide Monomers," Journal of Polymer Science Part C, Polymer Letters, Aug. 1969, vol. 7, No. 8, pp. 597-603.
Wuts, Greene's Protective Groups in Organic Synthesis, 554-684 (2014).
International Search Report for PCT International Application No. PCT/US2016/015331, dated Apr. 25, 2016, 4 pages.

*Primary Examiner* — Michael F Pepitone
*Assistant Examiner* — Jessica M Roswell
(74) *Attorney, Agent, or Firm* — Kent S. Kokko

(57) ABSTRACT

Protected photocrosslinkers and their use in two-stage photocuring of (meth)acrylate monomers is described.

19 Claims, No Drawings

ACRYLIC ADHESIVE COMPOSITION FROM PROTECTED PHOTOCROSSLINKING AGENTS

CROSS REFERENCE TO RELATED APPLICATIONS

This application is a national stage filing under 35 U.S.C. 371 of PCT/US2016/015331, filed Jan. 28, 2016, which claims the benefit of U.S. Application No. 62/117,636, filed Feb. 18, 2015, the disclosure of which is incorporated by reference in its/their entirety herein.

BACKGROUND

Pressure-sensitive tapes are virtually ubiquitous in the home and workplace. In its simplest configuration, a pressure-sensitive tape comprises an adhesive and a backing, and the overall construction is tacky at the use temperature and adheres to a variety of substrates using only moderate pressure to form the bond. In this fashion, pressure-sensitive tapes constitute a complete, self-contained bonding system.

According to the Pressure-Sensitive Tape Council, pressure-sensitive adhesives (PSAs) are known to possess properties including the following: (1) aggressive and permanent tack, (2) adherence with no more than finger pressure, (3) sufficient ability to hold onto an adherend, and (4) sufficient cohesive strength to be removed cleanly from the adherend. Materials that have been found to function well as PSAs include polymers designed and formulated to exhibit the requisite viscoelastic properties resulting in a desired balance of tack, peel adhesion, and shear holding power. PSAs are characterized by being normally tacky at room temperature (e.g., 20° C.). PSAs do not embrace compositions merely because they are sticky or adhere to a surface.

These requirements are assessed generally by means of tests which are designed to individually measure tack, adhesion (peel strength), and cohesion (shear holding power), as noted in A. V. Pocius in Adhesion and Adhesives Technology: An Introduction, $2^{nd}$ Ed., Hanser Gardner Publication, Cincinnati, Ohio, 2002. These measurements taken together constitute the balance of properties often used to characterize a PSA.

Solvent-processed acrylic PSA compositions can be crosslinked by adding a polyfunctional crosslinking compound that reacts with a reactive group present in the polymer. Hot melt coating a PSA composition eliminates the necessity of solvent processing. To hot melt process an adhesive composition, the composition must not be crosslinked before and during the coating process; however, to achieve a PSA with balanced properties (i.e., peel and shear adhesion), the composition eventually must be crosslinked. In hot melt coating processes, this is usually done by exposure to high energy radiation (e.g., E-beam or high intensity ultraviolet radiation). Commonly, when high intensity ultraviolet radiation is used, a photoactive crosslinking species such as benzophenone is added to the composition after an initial thermal polymerization.

SUMMARY

The present disclosure provides novel protected photocrosslinkers that may be added to a monomer mixture and are incorporated into the resulting polymer. These protected photocrosslinkers may then be deprotected and the polymers crosslinked.

The disclosure provides a method of making acrylate adhesives by photopolymerizing a monomer mixture containing a protected photocrosslinker, deprotecting the photocrosslinker, and photocrosslinking.

The protected photocrosslinkers enable a two-stage photocuring of acrylate monomers by a first stage of photopolymerization, followed by a second stage of photocrosslinking. The present method overcomes previous methods which required a first thermal polymerization step to avoid photocrosslinking and gellation of the polymer.

The present method further enables a first stage where the monomer mixture may be photopolymerized to a coatable viscosity, coated on a substrate, then photocrosslinked to provide an adhesive article having a layer of crosslinked acrylic adhesive.

In another aspect, the present disclosure provides a crosslinkable composition comprising an photocrosslinker-functional (meth)acrylate copolymer. The instant photocrosslinker-functional (meth)acrylate copolymer may be prepared by deprotecting a protected photocrosslinker-functional (meth)acrylate copolymer, which may in turn be prepared by incorporating a carbonyl-protected photocrosslinker into the copolymer.

As used herein:

"(meth)acrylate" or "acrylic" is a shorthand reference to acrylate, methacrylate, or combinations thereof; "(meth) acrylic" is a shorthand reference to acrylic, methacrylic, or combinations thereof; and "(meth)acryloyl" is a shorthand reference to acryloyl, methacryloyl, or combinations thereof.

"acryloyl" is used in a generic sense and mean not only derivatives of acrylic acid, but also amine, and alcohol derivatives, respectively;

"(meth)acryloyl" includes both acryloyl and methacryloyl groups; i.e. is inclusive of both esters and amides.

"alkyl" includes straight-chained, branched, and cycloalkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl, and the like. Unless otherwise noted, alkyl groups may be mono- or polyvalent, i.e monvalent alkyl or polyvalent alkylene.

"heteroalkyl" includes both straight-chained, branched, and cyclic alkyl groups with one or more heteroatoms independently selected from S, O, and N with both unsubstituted and substituted alkyl groups. Unless otherwise indicated, the heteroalkyl groups typically contain from 1 to 20 carbon atoms. "Heteroalkyl" is a subset of "hydrocarbyl containing one or more S, N, O, P, or Si atoms" described below. Examples of "heteroalkyl" as used herein include, but are not limited to, methoxy, ethoxy, propoxy, 3,6-dioxaheptyl, 3-(trimethylsilyl)-propyl, 4-dimethylaminobutyl, and the like. Unless otherwise noted, heteroalkyl groups may be mono- or polyvalent, i.e. monovalent heteroalkyl or polyvalent heteroalkylene.

"aryl" is an aromatic group containing 5-18 ring atoms and can contain optional fused rings, which may be saturated, unsaturated, or aromatic. Examples of an aryl groups include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl groups are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent, i.e. monovalent aryl or polyvalent arylene.

"hydrocarbyl" is inclusive of alkyl and aryl groups, including alkyl-substituted aryl groups (alkaryl) and aryl substituted alkyl groups (aralkyl).

"(hetero)hydrocarbyl" is inclusive of hydrocarbyl alkyl and aryl groups, and heterohydrocarbyl heteroalkyl and heteroaryl groups, the later comprising one or more catenary (in-chain) oxygen heteroatoms such as ether or amino groups.

Heterohydrocarbyl may optionally contain one or more catenary (in-chain) functional groups including ester, amide, urea, urethane, and carbonate functional groups. Unless otherwise indicated, the non-polymeric (hetero)hydrocarbyl groups typically contain from 1 to 60 carbon atoms. Some examples of such heterohydrocarbyls as used herein include, but are not limited to, methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl", and "heteroaryl" supr

DETAILED DESCRIPTION

The protected photocrosslinker is of the formula:

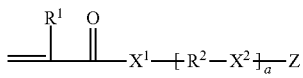
I wherein
$R^1$ is H or $CH_3$;
Each of $X^1$ and $X^2$ is —O— or —$NR^1$—;
$R^2$ is a divalent (hetero)hydrocarbyl group;
subscript a is 0 or 1,
Z is a carbonyl-protected chromophore that when deprotected will undergo Norrish Type I or Type II cleavage and crosslink the acrylic polymer.

The protecting groups may be any known in the art, and which render the photocrosslinker group non-photoactive upon protection. Reference may be made to P.G.M. Wuts, *Greene's Protective Groups in Organic Synthesis*, 5th Edition, Wiley Interscience, N.Y., pp 554-684. Useful carbonyl protecting groups may be selected from ketals (including cyclic ketals), dithioketals, O-substituted cyanohydrins, substituted hydrazones, oxazolidines, imidazolidines acylals, imines (derived from primary amines such as aniline and benzylamine) and thiazolidines. Most preferred are those protecting groups that may be cleaved with water and catalytic acid, such as ketals. Following a preparation of the photocrosslinker, the carbonyl group is protected to render in non-photoactive.

In one embodiment, Z can be a protected radiation sensitive aryl ketone group capable of Norrish Type I cleavage (α-cleavage). Such α-cleavage photoinitiator groups are particularly suited for syrup polymer compositions. Basic photochemistry of aryl ketones is discussed in a text by J. G. Calvert and J. N. Pitts, Jr., "Photochemistry" John Wiley & Sons, Inc., New York (1966). Preferably Z is selected from protected photoactive (radiation sensitive) groups having the formula:

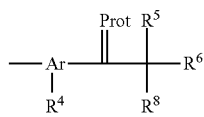

in which Ar is an arylene group having 5 to 18 carbon atoms that can be substituted by a lower alkyl group having one to six carbon atoms, and may contain 1-3 heteroatoms, Ar is preferably selected from phenylene, naphthalene, and biphenylene;

Prot is a protecting group on the carbonyl, such as ketal;
$R^4$ is selected from the group consisting of hydrogen, $C_1$ to $C_{12}$ alkyl groups, $C_1$ to $C_{12}$ alkoxy groups, and phenyl groups;

$R^5$, $R^6$, and $R^8$ independently are selected from the group consisting of hydroxyl, $C_1$ to $C_{12}$ alkyl groups, $C_1$ to $C_{12}$ alkoxy groups, di($C_1$ to $C_{12}$ alkyl substituted) amino groups, and aryl groups, provided that at least one of $R^5$, $R^6$ and $R^8$ is selected from the group consisting of hydroxyl, $C_1$ to $C_{12}$ alkoxy groups, or di $C_1$ to $C_{12}$ alkyl substituted amino groups, or that any two of $R^5$, $R^6$, and $R^8$ together can be an alkylene group, —$(C_qH_{2q})$—, or an alkylene-dioxy group, —O—$(C_qH_{2q})$—O—, in which q is an integer having a value of two or three, that together with the carbon atoms to which they are attached to form a 5- or 6-membered ring, or any two of $R^5$, $R^6$, and $R^8$ taken together with the carbon atom to which they are attached can form a carbonyl group —CO— provided that the remaining $R^5$, $R^6$, and $R^8$ is selected from the group consisting of hydroxyl, $C_1$ to $C_{12}$ alkoxy groups, di $C_1$ to $C_{12}$ alkyl substituted amino groups, and aryl groups.

Examples of α-cleavage photocrosslinker groups corresponding to Z may be represented by the following structures. Such groups are substituted with the —$(X^2—R^2)_a$—$X^1$—H at the open valence and n is 0 or 1.

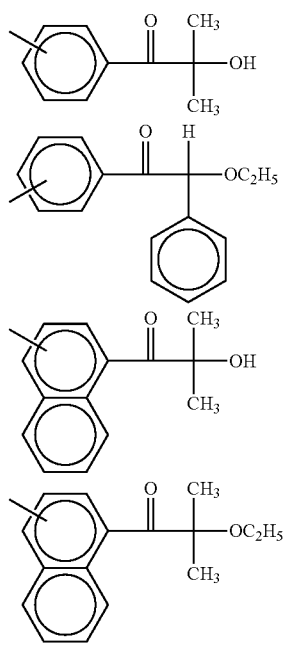

-continued

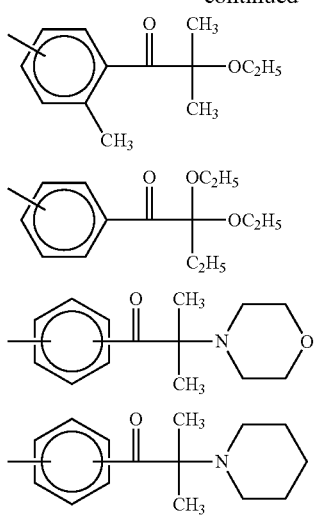

In another embodiment the photoinitiator group Z may be selected from a carbonyl-protected hydrogen abstraction-type photoinitiator group. Such groups may be derived from a benzophenone, anthraquinone, 9-fluorenone, anthrone, xanthone, thioxanthone, acridone, dibenzosuberone, chromone, flavone, benzyl, and acetophenone compounds substituted by a nucleophilic $H-X^1-(R^2-X^2)_n-$ group at the open valence. Such groups may be represented by:
Redraw

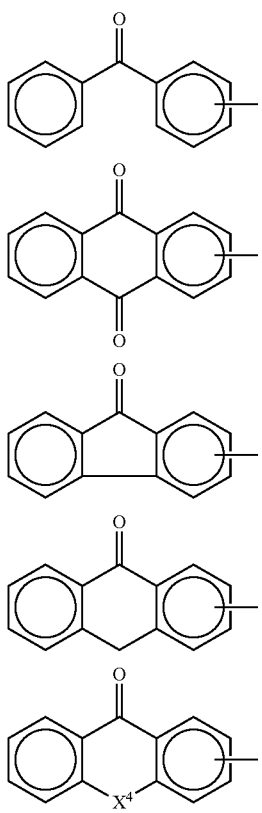

$X^4 = O$, S or NH

-continued

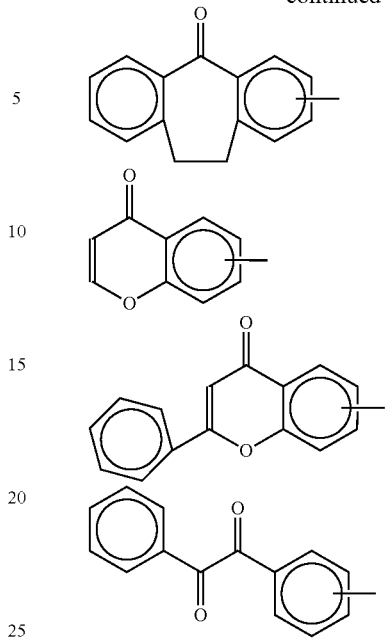

Preferably, Z is derived from protected, preferably ketal-protected acetophenone, benzophenone, anthraquinone, 9-fluorenone, anthrone, xanthone, thioxanthone, acridone, dibenzosuberone, benzil, chromone, benzoyl cyclohexane, benzoyl piperidine, benzoyl piperazine, benzoyl morpholine, benzoyl tert-alkylene, and benzoyl-tert-hydroxyalkylene.

In general, the protected photocrosslinkers may be prepared by (meth)acylation of a photocrosslinker compound having a nucleophilic group, followed by protection of the carbonyl groups, rendering the compound photopolymerizable, but not photoactive. Alternatively, the photocrosslinker compound may be carbonyl-protected, followed by acylation.

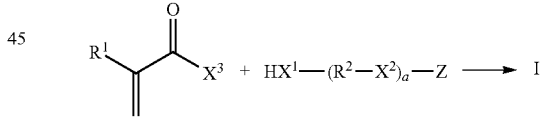

where $X^3$ is a leaving group, such as a halide or alkoxy, that may be displaced by the $HX^1-$,
$X^1$ and $X^2$ are independently $-O-$ or $-NH-$;
$R^2$ is a divalent alkylene of 2 to 10 carbon atoms or $-(R^3)_2C(CH_2)_m(CO)OR^9-$, where m is 0 or 1, $R^3$ is H or a $C_1$ to $C_4$ alkyl group, and $R^9$ is a $C_2$-$C_6$ alkylene;
$R^1$ is H or $CH_3$; and
Z is a photocrosslinker group.

The carbonyl of the Z group may be protected before or after acylation. With certain amine containing protecting groups, such as substituted hydrazones, Michael addition to the acrylate will compete with protection of the carbonyl, and therefore the carbonyl is protected prior to acylation. With other protecting groups, such as ketals, the carbonyl is preferably protected after acylation. Simple ketals may be prepared by reaction with an ortho-ester such as $(MeO)_3CH$ with an acid catalyst, and may be subsequently cleaved by hydrolysis. Cyclic ketals may be prepared from diols.

The photoactive crosslinking compound of Formula I can be prepared by the ring-opening of an electrophilic 2-alkenyl azlactone compound with a nucleophilic H—$X^1$—($R^2$—$X^2$)$_n$— group substituted photocrosslinker compound. Reference may be made to U.S. Pat. No. 5,505,279 (Gaddam et al.). Suitable nucleophiles include hydroxyl, primary amine, secondary amine, and thiol groups. The photocrosslinkers derived from 2-alkenyl azlactone compounds yield photocrosslinkers of Formula I where $X^1$—$R^2$—$X^2$ is —NH—C($CH_3$)$_2$—CO—O—($R^{10}$—O)$_b$—, where $R^{10}$ is a linear or branched alkylene, and subscript b is 0 or 1.

A significant advantage of using the 2-alkenyl azlactone instead of acryloyl chloride as an acylating agent is that the azlactone nucleophile reaction involves ring-opening addition; no smaller by-product molecule (such as hydrogen chloride) is displaced or generated in the reaction.

Alkenyl azlactones can be prepared by methods well known in the art. See, e.g., Iwakura et al., *Tetrahedron*, 23, 3363 (1967); Hubner et al., *Makromol. Chem.*, 11, 109 (1970); Taylor et al., *J. Poly. Sci., Poly. Let. Ed.*, 7, 597 (1969); and U.S. Pat. Nos. 4,304,705 and 4,777,276. These methods involve subjecting an amino acid having the general formula $H_2N(CH_2)_mC(R^3)_2COOH$ (wherein m and $R^3$ are defined as above) to acylation with an ethylenically unsaturated acylating agent having the general formula $H_2C=CR^7C(O)Cl$ (wherein $R^7$ is defined as above) using the method described by, for example, Kulkari et al., *J. Poly. Sci.*, 54, 491 (1961) in which the acylating agent (preferably containing a polymerization inhibitor such as hydroquinone) and an equivalent amount of an acid absorber (e.g., aqueous NaOH) are added portionwise to a chilled (e.g., 0° C.), vigorously stirred aqueous solution of an equimolar amount of an alkali metal salt of the amino acid, followed by neutralization with an aqueous acid (e.g., 6 N HCl), and isolation of the unsaturated peptide carboxylic acid product. This product is then dehydrated by introduction of a dehydrating agent (such as, for example, acetic anhydride, ethyl chloroformate, or dicyclohexylcarbodiimide) to give a 2-alkenyl azlactone.

Nucleophile substituted photocrosslinker compounds that can be used in the present disclosure include benzophenone, anthraquinone, 9-fluorenone, anthrone, xanthone, thioxanthone, acridone, dibenzosuberone, chromone, flavone, benzyl, and acetophenone compounds having a nucleophilic H—$X^1$—($R^2$—$X^2$)$_n$— group thereon. This may be exemplified by the benzophenone compound:

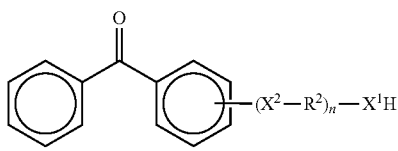

The benzophenone photocrosslinker may be of the following of the formula, where the —$X^1$—($R^2$—$X^2$)$_a$— link is not shown:

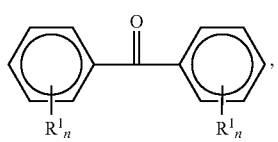

wherein each $R^1$ is independently selected from $C_1$-$C_{12}$ alkyl, $C_1$-$C_{12}$ alkyloxy, $C_1$-$C_{12}$ alkylthio, aryl, aryloxy, arylthio, nitrile and halide.

Specific examples of monofunctional benzophenones include benzophenone, 4-phenylbenzophenone, 4-methoxybenzophenone, 4,4'-dimethoxybenzophenone, 4,4'-dimethylbenzophenone, 4-methylbenzophenone, 4-(2-hydroxyethylthio)-benzophenone, and 4-(4-tolylthio)-benzophenone.

The anthraquinone photocrosslinker is of the formula, where the —$X^1$—($R^2$—$X^2$)$_a$— link is not shown:

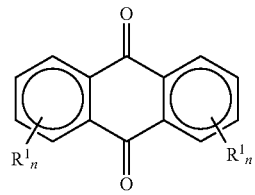

where each $R^1$ is independently selected from $C_1$-$C_{12}$ alkyl, $C_1$-$C_{12}$ alkyloxy, $C_1$-$C_{12}$ alkylthio, aryl, aryloxy, arylthio, nitrile and halide, and n is 0 to 4.

Representative examples of useful anthraquinone photocrosslinkers include anthraquinone, 2-methyl anthraquinone, 2-t-butyl anthraquinone, 2-ethyl anthraquinone, 2-phenyl anthraquinone, 1,4-dimethyl anthraquinone, 2,3-dimethyl anthraqinone, 1,2-dimethyl anthraqinone, 1-methoxy-2-methyl anthraquinone, 2-acetyl anthraquinone, and 2,6-di-t-butyl anthraquinone.

The thioxanthone photocrosslinker is of the formula, where the —$X^1$—($R^2$—$X^2$)$_a$— link is not shown:

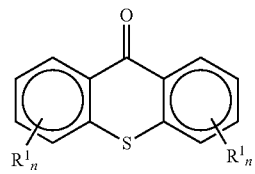

where each $R^1$ is independently selected from $C_1$-$C_{12}$ alkyl, $C_1$-$C_{12}$ alkyloxy, $C_1$-$C_{12}$ alkylthio, aryl, aryloxy, arylthio, nitrile and halide, and n is 0 to 4.

Representative examples of useful thioxanthone photocrosslinkers include thioxanthone, 2-isopropylthioxanthone, 2-chlorothioxanthone, 2-dodecylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone-1-ethoxycarbonyl-3-(1-methyl-1-morpholinoethyl)-thioxanthone, 2-methyl-6-dimethoxymethylthioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 6-ethoxycarbonyl-2-methoxythioxanthone, and 6-ethoxycarbonyl-2-methylthioxanthone Particularly preferred is 2-isopropylthioxanthone. Other preferred thioxanthones include 1-chloro-4-propoxythioxanthone, 2-propoxythioxanthone, and 4-propoxythioxanthone.

Other useful benzophenone, thioxanthone and anthraquinone chromophores are described in U.S. Pat. No. 6,235,922 (Heilmann et al).

The amount and identity of the crosslinker is a function of the amount of the photocrosslinker incorporated into the copolymer and is tailored depending upon application of the adhesive composition. Typically, the photocrosslinking agent is present in amounts less than 5 parts based on total dry weight of adhesive composition. More specifically, the photocrosslinker may be present in amounts from 0.01 to 5 parts, preferably 0.05 to 1 parts, based on 100 parts total monomers used.

The ability to vary the crosslink density permits the modification of properties suitable for the various applications described previously. The novel compositions of the present invention cure to form crosslinked compositions possessing tailorable properties such as shear, peel, release, strength, hardness, elasticity, absorbancy and toughness, for example, through selection of the particular constituents, and by control of the crosslink density. While the requirements for medical gels and flexible coatings, for example, may be different, the structure of the material and density of linkages can be altered while still maintaining the same method of forming crosslinked compositions. The maximum crosslink density is predetermined by the percentage of polymerizable functional groups and pendent photoinitiator groups incorporated into the crosslinkable composition. It may also be desirable to partially convert or cure a system for improved processing, while using a subsequent curing stage to obtain final properties.

When the photocrosslinker group is a hydrogen abstraction-type, the crosslinking compound is generally used in amounts of 0.01 to 0.5 parts by weight, preferably 0.05 to 0.5 parts by weight. When the photoinitiator group is alpha-cleavage-type, the crosslinking compound is generally used in amounts of 0.1 to 3 parts by weight, preferably 0.5 to 2 parts by weight, relative to 100 parts total monomer.

The protected crosslinkers of the present disclosure can be used in the preparation of adhesives, including hot-melt and pressure-sensitive adhesives. This can be accomplished by mixing from about 0.01 to about 5 parts by weight (pbw) of a photoactive crosslinking compound relative to 100 pbw of (meth)acrylate copolymer or monomer mixture therefore. This can be done in either the extant polymer or the partially polymerized monomer-polymer syrup.

The present disclosure provides a pre-adhesive composition comprising an functional (meth)acrylate copolymer having pendent, protected photocrosslinker groups derived from the protected photocrosslinker of Formula I. The pendent, protected photocrosslinker groups may be deprotected, by for example hydrolysis of ketal protecting groups, and the copolymer crosslinked to provide a pressure-sensitive adhesive and pressure-sensitive adhesive articles.

The (meth)acrylate ester monomer useful in preparing the acid functional (meth)acrylate adhesive copolymer is a monomeric (meth)acrylic ester of a non-tertiary alcohol, which alcohol contains from 1 to 14 carbon atoms and preferably an average of from 4 to 12 carbon atoms.

Examples of monomers suitable for use as the (meth)acrylate ester monomer include the esters of either acrylic acid or methacrylic acid with non-tertiary alcohols such as ethanol, 1-propanol, 2-propanol, 1-butanol, 2-butanol, 1-pentanol, 2-pentanol, 3-pentanol, 2-methyl-1-butanol, 3-methyl-1-butanol, 1-hexanol, 2-hexanol, 2-methyl-1-pentanol, 3-methyl-1-pentanol, 2-ethyl-1-butanol, 3,5,5-trimethyl-1-hexanol, 3-heptanol, 1-octanol, 2-octanol, isooctyl-alcohol, 2-ethyl-1-hexanol, 3,7-dimethylheptanol, 3,7-dimethylhept-3-eneol, 1-decanol, 1-dodecanol, 1-tridecanol, 1-tetradecanol, citronellol, dihydrocitronellol, and the like. In some embodiments, the preferred (meth)acrylate ester monomer is the ester of (meth)acrylic acid with butyl alcohol or isooctyl alcohol, or a combination thereof, although combinations of two or more different (meth)acrylate ester monomer are suitable. In some embodiments, the preferred (meth)acrylate ester monomer is the ester of (meth)acrylic acid with an alcohol derived from a renewable source, such as 2-octanol, citronellol, dihydrocitronellol.

The (meth)acrylate ester monomer is present in an amount of 85 to 99 parts by weight based on 100 parts total monomer content used to prepare the polymer. Preferably (meth)acrylate ester monomer is present in an amount of 90 to 95 parts by weight based on 100 parts total monomer content.

The polymer further comprises an acid functional monomer, where the acid functional group may be an acid per se, such as a carboxylic acid, or a portion may be salt thereof, such as an alkali metal carboxylate. Useful acid functional monomers include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrene sulfonic acid, 2-acrylamido-2-methylpropanesulfonic acid, vinylphosphonic acid, and mixtures thereof.

Due to their availability, acid functional monomers of the acid functional copolymer are generally selected from ethylenically unsaturated carboxylic acids, i.e. (meth)acrylic acids. When even stronger acids are desired, acidic monomers include the ethylenically unsaturated sulfonic acids and ethylenically unsaturated phosphonic acids may be used. The acid functional monomer is generally used in amounts of 1 to 15 parts by weight, preferably 1 to 10 parts by weight, based on 100 parts by weight total monomer.

Representative examples of suitable non-acid functional polar monomers include but are not limited to 2-hydroxyethyl (meth)acrylate; N-vinylpyrrolidone; N-vinylcaprolactam; acrylamide; mono- or di-N-alkyl substituted acrylamide; t-butyl acrylamide; dimethylaminoethyl acrylamide; N-octyl acrylamide; poly(alkoxyalkyl) (meth)acrylates including 2-(2-ethoxyethoxy)ethyl (meth)acrylate, 2-ethoxyethyl (meth)acrylate, 2-methoxyethoxyethyl (meth)acrylate, 2-methoxyethyl methacrylate, polyethylene glycol mono(meth)acrylates; alkyl vinyl ethers, including vinyl methyl ether; and mixtures thereof. Preferred polar monomers include those selected from the group consisting of 2-hydroxyethyl (meth)acrylate and N-vinylpyrrolidinone.

The polar monomer may be present in amounts of 0 to <50 parts by weight, preferably 1 to 5 parts by weight, based on 100 parts by weight total monomer.

The monomer mixture may comprise:
a) 50-99 parts by weight of (meth)acrylate ester monomers;
b) 1-50 parts by weight of polar monomers, inclusive of acid-functional monomers;
  wherein the sum of the monomers is 100 parts by weight.

In other embodiments the (meth)acrylate monomer comprises:
a) 50-99 parts by weight of (meth)acrylate ester monomers;
b) 1-15 parts by weight of acid-functional monomers;

c) 0 to <50 parts by weight of polar monomers, exclusive of acid-functional monomers,
wherein the sum of the monomers is 100 parts by weight.

When used, vinyl monomers useful in the (meth)acrylate polymer include vinyl esters (e.g., vinyl acetate and vinyl propionate), styrene, substituted styrene (e.g., α-methyl styrene), vinyl halide, and mixtures thereof. Such vinyl monomers are generally used at 0 to 5 parts by weight, preferably 1 to 5 parts by weight, based on 100 parts by weight total monomer.

In order to increase cohesive strength of the coated adhesive composition, a multifunctional (meth)acrylate may be incorporated into the blend of polymerizable monomers. Multifunctional acrylates are particularly useful for emulsion or syrup polymerization. Examples of useful multifunctional (meth)acrylate include, but are not limited to, di(meth)acrylates, tri(meth)acrylates, and tetra(meth)acrylates, such as 1,6-hexanediol di(meth)acrylate, poly(ethylene glycol) di(meth)acrylates, polybutadiene di(meth)acrylate, polyurethane di(meth)acrylates, and propoxylated glycerin tri(meth)acrylate, and mixtures thereof. The amount and identity of multifunctional (meth)acrylate is tailored depending upon application of the adhesive composition. Typically, the multifunctional (meth)acrylate is present in amounts less than 5 parts based on total dry weight of adhesive composition. Such multifunctional (meth)acrylates are normally added after the first photopolymerization. More specifically, the multifunctional (meth)acrylate may be present in amounts from 0.01 parts to 1 part based on 100 parts total monomers of the adhesive composition.

The copolymerizable monomer mixture may optionally further comprise chain transfer agents to control the molecular weight of the resultant polymer. Examples of useful chain transfer agents include but are not limited to those selected from the group consisting of carbon tetrabromide, alcohols, mercaptans, and mixtures thereof. When present, the preferred chain transfer agents are isooctylthioglycolate and carbon tetrabromide. The emulsion mixture may further comprise up to about 0.5 parts by weight of a chain transfer agent, typically about 0.01 to about 0.5 parts by weight, if used, preferably about 0.05 parts by weight to about 0.2 parts by weight, based upon 100 parts by weight of the total monomer mixture.

The copolymers are generally prepared by a first stage of photopolymerization of the monomer mixture containing the protected photocrosslinker and a photoinitiator. Useful photoinitiators include substituted acetophenones such as benzyl dimethyl ketal and 1-hydroxycyclohexyl phenyl ketone, substituted alpha-ketols such as 2-methyl-2-hydroxypropiophenone, benzoin ethers such as benzoin methyl ether, benzoin isopropyl ether, substituted benzoin ethers such as anisoin methyl ether, aromatic sulfonyl chlorides, and photoactive oximes. The photoinitiator may be used in an amount from about 0.001 to about 5.0 parts by weight per 100 parts of total monomer (or polymer), preferably from about 0.01 to about 5.0 parts by weight per 100 parts of total monomer, and more preferably in an amount from 0.1 to 0.5 parts by weight per 100 parts of total monomer.

The resultant polymerization reaction product is an acid-functional (meth)acrylate copolymer having pendent, protected photoactive crosslinking side chains that comprise the protected radiation-sensitive photocrosslinker groups. These may be subsequently deprotected, activatable by UV radiation, resulting in a crosslinked adhesive product.

The first stage of photopolymerization produces a non-crosslinked copolymer. The monomers may fully or partially converted. The degree of conversion of monomers in the first photopolymerization step can be monitored during the irradiation by measuring the index of refraction of the polymerizing medium. In some embodiments the monomer mixture is converted to a useful coating viscosity suitable for coating a substrate. Useful coating viscosities are achieved with conversions (i.e. the percentage of available monomer polymerized) in the range of up to 50%, preferably 2-30%, more preferably from 5-20%. The molecular weight (weight average) of the solute copolymer(s) is at least 100,000, preferably at least 500,000.

The copolymer may be represented by the following formula. Subsequently the carbonyl-protected MPX* monomer unit are deprotected to yield the photoactive MPX monomer units.

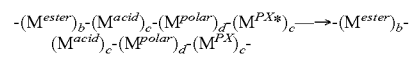

where
$M^{ester}$ represents polymerized monomer units derived from (meth)acrylate monomers,
$M^{acid}$ represents polymerized monomer units derived from acid functional monomers
$M^{polar}$ represents polymerized monomer units derived from non-acid functional polar monomers,
$M^{PX}$* represents polymerized monomer units derived from the protected photocrosslinker monomers,
$M^{PX}$ represents polymerized monomer units derived from the deprotected photocrosslinker monomers, and
subscripts b, c, d and e represent the parts by weight of each monomer in the copolymer as previously described.

In one preferred embodiment, the $M^{PX}$* monomer units may be ketal protected benzophenone, which may be deprotected by hydrolysis to the photoactive benzophenone.

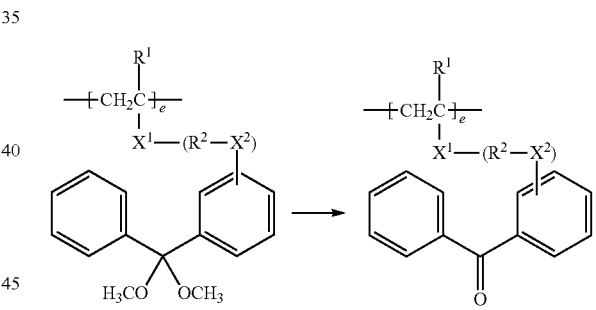

In one embodiment the present disclosure provides method of preparing a pressure sensitive adhesive comprising partially polymerizing monomers to produce a syrup polymer comprising the protected photocrosslinker—functional (meth)acrylate solute copolymer and unpolymerized solvent monomers. The carbonyl group of the "Z" group may be deprotected and the syrup polymer further polymerized and crosslinked.

It will be understood that the first photopolymerization step to produce the uncrosslinked copolymer will produce a "dead polymer" in the initial photopolymerization; i.e. a fully polymerized, not free-radically polymerizable polymer. Subsequently the solvent monomer mixture does not free-radically polymerize onto the extant copolymer, although the two copolymers may be subsequently crosslinked.

The photoinitiator group Z of Formula I is preferably selected as an α-cleavage type photocrosslinker to the efficiently crosslink the resulting copolymer and may photopolymerize the remaining monomers.

Partial polymerization provides a coatable solution of the protected photocrosslinker-functional (meth)acrylate solute copolymer in one or more solvent monomers. For syrup application processing, a preferred monomer mixture comprises 85 to 99 pbw of one or more (meth)acrylate ester monomers, 1 to 15 pbw of acid functional monomers, 0 to 10 pbw of one or more second, non-acid, polar monomers, and 0 to about 5 pbw of other vinyl monomers, based on 100 parts total monomer.

In some embodiments, the initial photopolymerization may be followed by a thermal polymerization. That is, this disclosure provides a method of preparing an adhesive comprising the steps of
1) photopolymerizing a monomer mixture to provide a syrup polymer composition comprising a solute copolymer having pendent, protected photocrosslinking groups;
2) thermally polymerizing the syrup to produce a copolymer composition wherein the photocrosslinking groups are deprotected;
3) optionally coating the copolymer composition of step 2); and
4) photocrosslinking the copolymer composition.

The first step of photopolymerization may be to any desired degree of conversion, as previously described.

A thermal initiator may be added to the initial monomer mixture of step 1) provided that the temperature is controlled to avoid thermal initiation. Preferably the thermal initiator is added to the syrup copolymer composition product of step 1), and at least 95 wt. % of the solvent monomers are converted to copolymer. Unreacted monomers and other volatiles may be removed by means known in the art prior to the photocrosslinking step.

Suitable initiators include but are not limited to those selected from the group consisting of azo compounds such as VAZO™ 64 (2,2'-azobis(isobutyronitrile)) and VAZO™ 52 (2,2'-azobis(2,4-dimethylpentanenitrile)), peroxides such as benzoyl peroxide and lauroyl peroxide, The preferred thermal initiator Vazo 88 (1,1'-azobis(cyclohexanecarbonitrile)), Lupersol 101 (2,5-Bis(tert-butylperoxy)-2,5-dimethylhexane) and Lupersol 130 (2,5-dimethyl-2,5-di(t-butylperoxy)-3-hexyne.

When used, initiators may comprise from about 0.0005 to about 1 part by weight, preferably about 0.001 to about 0.5 part by weight based on 100 parts by weight of syrup polymer composition.

It has been observed that the second thermal polymerization step is sufficient to deprotect the protected photocrosslinker groups. It is believed that the ambient moisture and/or the residual moisture in the reactants is sufficient to hydrolyze the protecting groups catalyzed by the acid functionality of the copolymer.

Solventless polymerization methods, such as the continuous free radical polymerization method described in U.S. Pat. Nos. 4,619,979 and 4,843,134 (Kotnour et al.); the essentially adiabatic polymerization methods using a batch reactor described in U.S. Pat. No. 5,637,646 (Ellis); and, the methods described for polymerizing packaged pre-adhesive compositions described in U.S. Pat. No. 5,804,610 (Hamer et al.) may also be utilized to prepare the polymers. Preferably, the first copolymer is prepared by the adiabatic batch polymerization process wherein the total of the absolute value of any energy exchanged to or from the batch during the course of reaction will be less than about 15% of the total energy liberated due to reaction for the corresponding amount of polymerization that has occurred during the time that polymerization has occurred, as described in U.S. Pat. No. 5,637,646 (Ellis), incorporated herein by reference.

Preferably the components are combined and photopolymerized using the methods described in the methods described for polymerizing packaged pre-adhesive compositions described in WO9607522 (Hamer et al.) and in U.S. Pat. No. 5,804,610 (Hamer et al.), incorporated herein by reference.

In the methods of Hamer, the packaging material used to form the reaction vessel or container is preferably made of a material that when combined with the adhesive composition does not substantially adversely affect the desired adhesive characteristics. A hot melt coated adhesive produced from a mixture of the adhesive composition and the packaging material may have improved adhesive properties compared to a hot melt coated adhesive produced from the adhesive composition alone.

At least one component of the packaging material (more preferably the entirety of the packaging material) preferably melts at or below the processing temperature of the adhesive (i.e., the glass transition temperature $T_g$, at which the adhesive composition begins to flow). The packaging material preferably has a melting point of 200° C. or less, preferably 170° C. or less. In a preferred embodiment the melting point ranges from 90° C. to 150° C.

The packaging material should be appropriate for the polymerization method used. For example, with photopolymerization, it is necessary to use a film material that is sufficiently transparent to ultraviolet radiation at the wavelengths necessary to effect polymerization.

In another embodiment of the disclosure, a reaction mixture is coated onto a carrier web, covered with a sheet material, and polymerized, wherein the carrier web, the sheet material, or both, are hot melt coatable with the adhesive. If both the carrier web and the sheet material are hot melt coatable, the resulting composite can be fed directly into a hot melt coater, or cut into smaller strips or pieces and fed to the hot melt coater. If only one of the carrier web or the sheet material is hot melt-coatable with the adhesive, the non-coatable entity is removed before the adhesive is hot melt coated. To facilitate handling after the non-coatable entity is removed, the polymerized adhesive can be folded over onto itself so that the coatable entity substantially surrounds the major surfaces of the coated adhesive. The adhesive web can then be fed into a hot melt coater, or it can be cut to smaller strips or pieces before hot melt coating.

If either the carrier web or the sheet material are not coatable with the adhesive it should be treated, if necessary, so that the adhesive can be removed easily from it. Such treatments include silicone release coatings, polyfluoropolyether coatings, and polyfluoroethylene coatings such as Teflon™.

The carrier web should provide sufficient strength to support the coated reaction mixture during polymerization, or it can be supported by a platen during polymerization. The carrier web can be an endless conveyor belt, or it can be a flexible material which can be wound into a roll with the adhesive; the carrier web is itself a sheet material. Endless conveyor belts can be made from silicone elastomers; polymeric films such as those made from polyfluoroethylene, polyester, nylon, polycarbonate, and the like; metals such as stainless steel; rubber; glass fibers; and the like. Useful flexible materials include paper and polymeric films such as those made from polyester, nylon, polycarbonates, polyolefins, ethylene acrylic acid, ethylene vinyl acetate, ionomers, and the like. Coatable flexible materials include polyolefins such as polypropylene, polyethylene, and polybutadiene; ethylene acrylic acid; ethylene vinyl acetate; and ionomers.

Likewise, the sheet material can be made from the aforementioned flexible materials as well as non-flexible plates made of glass, polymers, or metals, which may optionally be coated with a release material. If the reaction mixture is to be subsequently photo-polymerized, the carrier web, the sheet material, or both should be sufficiently transparent to actinic radiation to effect such photopolymerization.

Preferably, the packaging material does not substantially adversely affect the adhesive properties of a hot melt coated mixture of the packaging material and an adhesive produced from polymerization of the reaction mixture, and a hot melt coated mixture of the adhesive and the packaging material preferably has a storage modulus when measured in torsional shear at 25° C. and at 1 radian/second of between about $10^3$ and about $10^7$ Pa.

The resultant polymerized blend may be further melt processed to produce a homogenous blend. Physical blending devices that provide dispersive mixing, distributive mixing, or a combination of dispersive and distributive mixing are useful in preparing homogenous blends. Both batch and continuous methods of physical blending can be used. Examples of batch methods include BRABENDER (using a BRABENDER PREP CENTER, available from C. W. Brabender Instruments, Inc.; South Hackensack, N.J.) or BANBURY internal mixing and roll milling (using equipment available from FARREL COMPANY; Ansonia, Conn.). Examples of continuous methods include single screw extruding, twin screw extruding, disk extruding, reciprocating single screw extruding, and pin barrel single screw extruding. The continuous methods can include utilizing both distributive elements, such as cavity transfer elements (e.g., CTM, available from RAPRA Technology, Ltd.; Shrewsbury, England) and pin mixing elements, static mixing elements and dispersive elements (e.g., MADDOCK mixing elements or SAXTON mixing elements as described in "Mixing in Single-Screw Extruders," *Mixing in Polymer Processing*, edited by Chris Rauwendaal (Marcel Dekker Inc.: New York (1991), pp. 129, 176-177, and 185-186).

Generally the molten, extrudable composition is metered into an extrusion die (e.g., a contact or drop die). The shape of the extruded composition is dictated by the shape of the exit opening of the die. Although a variety of shapes may be produced, the extruded composition is typically produced in the form of a continuous or discontinuous sheet. The extrusion die may be a drop die, contact die, profile die, annular die, or a casting die, for example, as described in Extrusion Dies: Design & Engineering Computation, Walter Michaelis, Hanser Publishers, New York, N.Y., 1984, which is incorporated herein by reference in its entirety.

If desired, the smoothness of one or both of the extrudate surfaces can be increased and the thickness reduced by using a nip roll to press the extrudate against a chill roll after the extruded composition exits the die. The thickness of the extruded sheet is preferably from about 0.001 mm to about 5 mm, and more preferably from 0.005 to 0.5 mm. If the sheet is too thin, handling of the adhesive sheet tends to become difficult, while if it is too thick, crosslinking becomes non-uniform in the direction of thickness, and this may reduce the reliability of the adhesive.

The extruded coating is typically deposited on a substrate. Thus, in another aspect, an article is provided. The article includes a substrate and a coating of the crosslinkable composition positioned adjacent to the substrate. The crosslinkable composition is the same as described supra. As used herein, the term "adjacent" refers to a first layer positioned near the second layer. The first and second layers can be in contact or can be separated from each other by another layer. For example, a substrate can be positioned adjacent to the crosslinkable composition if the substrate contacts the crosslinkable composition or is separated from the crosslinkable composition by another layer such as a primer layer or surface modification layer that increases the adhesion of the crosslinkable composition to the substrate. The crosslinkable composition is typically applied as a coating to a major surface of the substrate and the article is a substrate coated with the crosslinkable composition.

Any suitable substrate can be used in the article. For example, the substrate can be flexible or inflexible and can be formed from a polymeric material, glass or ceramic material, metal, or combination thereof. Some substrates are polymeric films such as those prepared from polyolefins (e.g., polyethylene, polypropylene, or copolymers thereof), polyurethanes, polyvinyl acetates, polyvinyl chlorides, polyesters (polyethylene terephthalate or polyethylene naphthalate), polycarbonates, polymethyl(meth)acrylates (PMMA), ethylene-vinyl acetate copolymers, and cellulosic materials (e.g., cellulose acetate, cellulose triacetate, and ethyl cellulose). Other substrates are metal foils, nonwoven materials (e.g., paper, cloth, nonwoven scrims), foams (e.g., polyacrylic, polyethylene, polyurethane, neoprene), and the like. For some substrates, it may be desirable to treat the surface to improve adhesion to the crosslinked composition, crosslinked composition, or both. Such treatments include, for example, application of primer layers, surface modification layer (e.g., corona treatment or surface abrasion), or both.

In some embodiments, the substrate is a release liner. Release liners typically have low affinity for the crosslinkable composition or crosslinked composition. Exemplary release liners can be prepared from paper (e.g., Kraft paper) or other types of polymeric material. Some release liners are coated with an outer layer of a release agent such as a silicone-containing material or a fluorocarbon-containing material.

The crosslinkable composition coating can have any desired thickness that can be effectively crosslinked when exposed to ultraviolet radiation. In many embodiments, the crosslinkable composition coating has a thickness no greater than 20 mils (500 micrometers), no greater than 10 mils (250 micrometers), no greater than 5 mils (125 micrometers), no greater than 4 mils (100 micrometers), no greater than 3 mils (75 micrometers), or no greater than 2 mils (50 micrometers). The thickness is often at least 0.5 mils (12.5 micrometers) or at least 1 mil (25 micrometers). For example, the thickness of the crosslinkable composition coating can be in the range of 0.5 mils (2.5 micrometers) to 20 mils (500 micrometers), in the range of 0.5 mils (5 micrometers) to 10 mils (250 micrometers), in the range of 0.5 mils (12.5 micrometers) to 5 mils (125 micrometers), in the range of 1 mil (25 micrometers) to 3 mils (75 micrometers), or in the range of 1 mil (25 micrometers) to 2 mils (50 micrometers).

In other aspects, a crosslinked composition and an article containing the crosslinked composition are provided. The crosslinked composition is the reaction product of a crosslinkable composition exposed to ultraviolet radiation. The article includes a substrate and a crosslinked composition coating positioned adjacent to the substrate. The substrate and the crosslinkable composition used to form the crosslinked composition are the same as described above. Suitable ultraviolet radiation sources are the same as described above.

The extruded composition may optionally be combined with a liner. Suitable materials for liner include silicone release liners, polyester films (e.g., polyethylene terephthalate films), and polyolefin films (e.g., polyethylene films). The liner and the extruded composition may be laminated together between a pair of nip rollers.

Preceding photocrosslinking, the carbonyl of the Z group is deprotected. It has been found that subsequent melt processing provides sufficient temperatures and ambient moisture to hydrolyze ketal protecting groups, so a separate hydrolysis step is not necessary. It has further been found that acid-functional monomers such as acrylic acid in the copolymer is a sufficient source of acid catalyst, so no additional acid is necessary for hydrolysis. The ketals may be deprotected be hydrolyzed in a separate step by exposure to water and an acid catalyst. Other protecting groups may be removed by means known in the art, such as described in Wuts supra.

The instant method requires a first step of photopolymerization and a second step of photocrosslinking initiated by UV. UV light sources can be of two types: 1) relatively low light intensity sources such as Blacklights which provide generally 10 mW/cm$^2$ or less (as measured in accordance with procedures approved by the United States National Institute of Standards and Technology as, for example, with a UVIMAP™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities generally greater than 10 mW/cm$^2$, preferably between 15 and 450 mW/cm$^2$. Where actinic radiation is used to fully or partially polymerize the syrup polymer composition, high intensities and short exposure times are preferred. For example, an intensity of 600 mW/cm$^2$ and an exposure time of about 1 second may be used successfully. Intensities can range from about 0.1 to about 150 mW/cm$^2$, preferably from about 0.5 to about 100 mW/cm$^2$, and more preferably from about 0.5 to about 50 mW/cm$^2$.

The UV sources may be the same or different for the photopolymerization and the photocrosslinking steps.

The adhesives may also contain one or more conventional additives. Preferred additives include tackifiers, plasticizers, dyes, antioxidants, and UV stabilizers. Such additives can be used if they do not affect the superior properties of the adhesives.

In some embodiments the composition includes a tackifier. Either solid or liquid tackifiers can be added. Solid tackifiers generally have a number average molecular weight (Mn) of 10,000 grams per mole or less and a softening point above about 70° C. Liquid tackifiers are viscous materials that have a softening point of about 0° C. to about 70° C.

Suitable tackifying resins include rosin resins such as rosin acids and their derivatives (e.g., rosin esters); terpene resins such as polyterpenes (e.g., alpha pinene-based resins, beta pinene-based resins, and limonene-based resins) and aromatic-modified polyterpene resins (e.g., phenol modified polyterpene resins); coumarone-indene resins; and petroleum-based hydrocarbon resins such as C5-based hydrocarbon resins, C9-based hydrocarbon resins, C5/C9-based hydrocarbon resins, and dicyclopentadiene-based resins. These tackifying resins, if added, can be hydrogenated to lower their color contribution to the pressure-sensitive adhesive composition. Combinations of various tackifiers can be used, if desired. In many embodiments, the tackifier is a rosin ester or includes a rosin ester.

Tackifiers that are rosin esters are the reaction products of various rosin acids and alcohols. These include, but are not limited to, methyl esters of rosin acids, triethylene glycol esters of rosin acids, glycerol esters of rosin acids, and pentaertytritol esters of rosin acids. These rosin esters can be hydrogenated partially or fully to improve stability and reduce their color contribution to the pressure-sensitive adhesive composition. The rosin resin tackifiers are commercially available, for example, from Eastman Chemical Company (Kingsport, Tenn., USA) under the trade designations PERMALYN, STAYBELITE, and FORAL as well as from Newport Industries (London, England) under the trade designations NUROZ and NUTAC. A fully hydrogenated rosin resin is commercially available, for example, from Eastman Chemical Company under the trade designation FORAL AX-E. A partially hydrogenated rosin resin is commercially available, for example, from Eastman Chemical Company under the trade designation STAYBELITE-E.

Tackifiers that are hydrocarbon resins can be prepared from various petroleum-based feed stocks. These feedstocks can be aliphatic hydrocarbons (mainly C5 monomers with some other monomers present such as a mixture of trans-1, 3-pentadiene, cis-1,3-pentadiene, 2-methyl-2-butene, dicyclopentadiene, cyclopentadiene, and cyclopentene), aromatic hydrocarbons (mainly C9 monomers with some other monomers present such as a mixture of vinyl toluenes, dicyclopenetadiene, indene, methylstyrene, styrene, and methylindenes), or mixtures thereof. Tackifiers derived from C5 monomers are referred to as C5-based hydrocarbon resins while those derived from C9 monomers are referred to as C9-based hydrocarbon resins. Some tackifiers are derived from a mixture of C5 and C9 monomers or are a blend of C5-based hydrocarbon tackifiers and C9-based hydrocarbon tackifiers. These tackifiers can be referred to as C5/C9-based hydrocarbon tackifiers. Any of these resins can be partially or fully hydrogenated to improve their color and thermal stability.

The C5-based hydrocarbon resins are commercially available from Eastman Chemical Company under the trade designations PICCOTAC and EASTOTAC, from Cray Valley (Exton, Pa., USA) under the trade designation WINGTACK, from Neville Chemical Company (Pittsburg, Pa., USA) under the trade designation NEVTAC LX, and from Kolon Industries, Inc. (South Korea) under the trade designation HIKOREZ. The C5-based hydrocarbon resins are commercially available from Eastman Chemical with various degrees of hydrogenation under the trade designation EASTOTACK.

The C9-based hydrocarbon resins are commercially available from Eastman Chemical Company under the trade designation PICCO, KRISTLEX, PLASTOLYN, and PICCOTAC, and ENDEX, from Cray Valley (Exton, Pa., USA) under the trade designations NORSOLENE, from Ruetgers N.V. (Belgium) under the trade designation NOVAREZ, and from Kolon Industries, Inc. (South Korea) under the trade designation HIKOTAC. These resins can be partially or fully hydrogenated. Prior to hydrogenation, the C9-based hydrocarbon resins are often about 40 percent aromatic as measured by proton Nuclear Magnetic Resonance. Hydrogenated C9-based hydrocarbon resins are commercially available, for example, from Eastman Chemical under the trade designations REGALITE and REGALREX that are 50 to 100 percent (e.g., 50 percent, 70 percent, 90 percent, and 100 percent) hydrogenated. The partially hydrogenated resins typically have some aromatic rings.

Various C5/C9-based hydrocarbon tackifiers are commercially available from Arakawa (Germany) under the trade designation ARKON, from Zeon Corporation (Japan) under the trade designation QUINTONE, from Exxon Mobile Chemical (Houston, Tex.) under the trade designation ESCOREZ, and from Newport Industries (London, England) under the trade designations NURES and H-REZ.

Any of the tackifiers may be used in an amount equal to at least 5 weight percent based on a total weight of solids in the composition. As used herein, the term "solids" includes all materials other than water and organic solvents in the crosslinkable composition. In some embodiments, the amount of tackifier is at least 10 weight percent, at least 20 weight percent, or at least 40 weight percent based on the total weight of solids in the crosslinkable composition. The amount of the tackifier can be up to and equivalent weight of the monomer/copolymer components. Generally the tackifier may be added in amounts of 60 weight percent or even higher, up to 55 weight percent, up to 50 weight percent, up to 45 weight percent, or up to 40 weight percent based on the total weight of the solids in the crosslinkable composition. In some embodiments, the tackifier is present in an amount in a range of 20 to 60 weight percent, in a range of 30 to 60 weight percent, in a range of 20 to 50 weight percent, in a range of 30 to 50 weight percent, in a range of 20 to 45 weight percent, or in a range of 20 to 40 weight percent based on the total weight of solids in the crosslinkable composition.

In some embodiments, such as when the composition comprises at tackifier, the crosslinked composition is typically a pressure-sensitive adhesive. Thus, articles with a coating of the crosslinked composition have a pressure-sensitive adhesive layer and can be used for many applications typical of such articles. The substrate adjacent to the pressure-sensitive layer can be selected depending on the particular application. For example, the substrate can be a sheeting material and the resulting article can provide decorative graphics or can be a reflective product. In other examples, the substrate can be label stock (the resulting article is a label with an adhesive layer) or tape backing (the resulting article is an adhesive tape). In yet other examples, the substrate can be a release liner and the resulting article can be a transfer tape. The transfer tape can be used to transfer the pressure-sensitive adhesive layer to another substrate or surface. Other substrates and surface include, for example, a panel (e.g., a metal panel such as an automotive panel) or a glass window.

Some articles are adhesive tapes. The adhesive tapes can be single-sided adhesive tapes with the crosslinkable composition attached to a single side of the tape backing or can be double-sided adhesive tape with a pressure-sensitive adhesive layer on both major surfaces of the tape backing. At least one of the two pressure-sensitive adhesive layers is the crosslinkable composition described above. Double-sided adhesive tapes are often carried on a release liner.

EXAMPLES

Test Methods
Determination of Adhesive Shear Strength:

Shear tests were conducted using 12.7 millimeter (mm) wide samples of adhesive tape prepared in the Examples. A stainless steel panel was cleaned by wiping with acetone and air drying. The samples of adhesive tape were applied to the panel such that a 25.4 mm by 25.4 mm portion of each adhesive tape was in firm contact with the panel and one end portion of each adhesive tape free (i.e., not attached to the panel). A 1000 gram weight was attached to the free end of the adhesive tape sample and the panel was held in a rack so that the panel formed an angle of 180° with the extended free end and the weight. The test was conducted at approximately 70° C. and the time elapsed in minutes for each adhesive tape to separate from the test panel was recorded as shear strength. If the time elapsed exceeded 10000 minutes, the time elapsed was recorded as >10000 minutes. Two shear tests were performed for each adhesive tape sample and the results averaged.

Determination of Peel Adhesion Force:

Peel adhesion force was measured using adhesive tapes prepared in the Examples. A stainless steel panel was cleaned by wiping with acetone and drying. Adhesive tapes measuring 12.7 mm wide by 10 to 12 cm long were adhered to the panel by rolling with a 2 kg hard rubber roller 2 times. The free end of the adhesive tape was doubled back so that the angle of removal was 180° and attached to the horizontal arm of an adhesion tester scale (SLIP/PEEL TESTER MODEL 3M90, obtained from Instrumentors Inc. Strongsville, Ohio, USA). The stainless steel plate was attached to the platform that moved at 12 inches per minute (30.5 centimeters per minute) away from the scale. The peel test was started immediately after the adhesive tape was applied to the test panel. The scale was read in ounces during the test as an average of the stabilized peel force. The number was then converted and reported as Newtons per decimeter (N/dm). Three peel tests were run for each sample and averaged to yield the reported peel force.

Determination of Gel Content:

A sample of the polymer (~0.30 gram) was placed onto center of a pre-weighed rectangular mesh (4 inch by 2.5 inch (~10 cm by 6.4 cm)). The mesh was MCNICHOLS QUALITY WIRE MESH (square weave, stainless steel type 304, woven construction, 325 mesh, 0.0014 inch (~36 micrometer) wire, 0.0017 inch (~43 micrometer) opening). The overhanging portion of the mesh was folded inwards to cover and immobilize the tape inside the mesh. The folded mesh with the enclosed polymer was immersed in 30 milliliters of toluene inside a glass jar for 24 hours. The mesh with the adhesive was then taken out of the jar and dried in an oven for 30 minutes at 120° C. and weighed again to calculate the sample mass. The gelled insoluble portion of the polymer was calculated as a gel weight percent ("gel wt. %") using the following equation.

$$\text{gel wt. \%} = \frac{\text{(final mass of mesh)}}{\text{(initial mass of mesh)}} \times 100$$

Determination of Inherent Viscosity (IV)

The inherent viscosities (IV) reported herein were obtained by conventional methods used by those skilled in the art. The IVs were obtained using a Lauda viscometer in a water bath controlled at 27° C., to measure the flow time of 10 ml of a polymer solution (0.3 g per deciliter polymer in ethyl acetate). The test procedure followed and the apparatus used were described in detail in Textbook of Polymer Science, F. W. Billmeyer, Wiley-Interscience, Second Edition, 1971, Pages 84 and 85.

Determination of Percent Solids

A sample (~0.5-2.0 grams) of test material was placed in a small tin open container and kept in a convection oven at approximately 105° C. overnight. By the measured weight loss of the evaporated monomer, the amount of monomer converted to polymer was calculated and expressed as a weight percent (wt. %).

TABLE 1

Materials

| Designation | Description | Source |
|---|---|---|
| IOA | Isooctyl acrylate | Sigma-Aldrich, St. Louis, MO |
| AA | Acrylic acid | Alfa Aesar, Heysham, England |
| IOTG | Isooctyl thioglycoate | Sigma-Aldrich, St. Louis, MO |
| AEBP | Acryloxyethoxybenzophenone | Prepared using a method similar to that described in U.S. Pat. No. 7,838,110 (Zhu et al.) |
| EVA film | A clear polyethylene vinyl acetate film, 0.065 millimeter thick, obtained from Flint Hills Resources under the trade designation "VA-24" | Flint Hills Resources, Wichita, KS |
| IRG651 | 2,2-Dimethoxy-2-phenylacetophenone, available from BASF under the trade designation "IRGACURE-651" | BASF, Florham Park, NJ |
| FORAL 3085 | A rosin ester available from Pinova under the trade designation "FORAL 3085" | Pinova, Brunswick, GA |
| TFA | Trifluoroacetic acid | Available from Sigma-Aldrich, St. Louis, MO |
| | Trimethylorthoformate | Available from Sigma-Aldrich, St. Louis, MO |

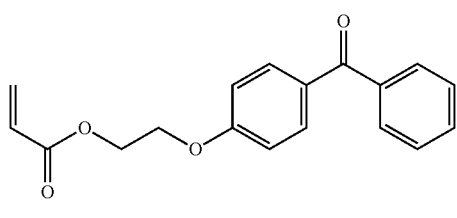

AEBP

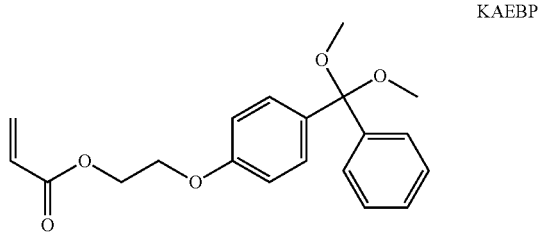

KAEBP

Example 1 (EX-1): Dimethyl Ketal of AEBP ("KAEBP")

AEBP was ketalized to form the corresponding dimethyl ketal ("KAEBP") by reaction with 25 eq. of MeOH, 1.5 eq. of trimethylorthoformate, and TFA at 20 mM. The reaction mixture was refluxed for 24 hours, then was stripped to dryness on a rotory evaporater. $^1$H NMR of the crude product showed a peak for methoxy groups at 3.01 ppm, and a 93.9% conversion of ketone to ketal by the ratio of a set of aromatic hydrogens at 7.85 ppm in the starting material relative to the peak at 7.47 ppm in the product. A portion of the crude KAEBP product was purified on a silica gel column, to provide the KAEBP as a viscous liquid.

Comparative Example 1 (CE-1)

A solution was prepared by blending IOA, AA, IOTG, and IRG651 in ajar, using the relative amounts shown in Table 2. To the mixture in the jar was added a magnetic stir bar, and the mixture was placed on a stir plate a mix, forming a curable composition. EVA film was heat sealed to form open ended receptacles each measuring 18 centimeters by 5 centimeters. Each receptacle was filled with approximately 26 grams of the curable composition. Air was forced out of the open end which was then heat sealed using a "MID-WEST PACIFIC IMPULSE SEALER" from J.J. Elemer Corp. (St. Louis, Mo., USA). The curable composition enclosed within the EVA film was immersed in a constant temperature water bath at 17° C. and irradiated with ultraviolet light (365 nm, 4 mW/cm$^2$) for eight minutes on each side to polymerize the curable composition.

TABLE 2

Curable Compositions

| | Base Monomers | | | | | |
|---|---|---|---|---|---|---|
| Sample | IOA, pbw | AA, pbw | AEBP, pbw | KAEBP*, pbw | IOTG, pbw | IRG651, pbw |
| CE-1 | 95 | 5 | 0 | 0 | 0.03 | 0.15 |
| CE-2 | 95 | 5 | 0.25 | 0 | 0.03 | 0.15 |
| EX-2 | 95 | 5 | 0 | 0.25 | 0.03 | 0.15 |
| EX-3 | 95 | 5 | 0 | 0.35 | 0.03 | 0.15 |

*The KAEBP that was used was the crude material obtained in PE-1 (i.e., ~94% purity)

Comparative Example 2 (CE-2)

Comparative Example 2 was made according to the procedure used for Comparative Example 2, except that the amounts of materials were as indicated for CE-2 in Table 2, including the 0.25 pbw of AEBP.

Example 2 (EX-2)

Example 2 was made according to the procedure used for Comparative Example 1, except that the amounts of materials were as indicated for EX-2 in Table 2, including the 0.25 pbw of KAEBP. Proton NMR showed that the methoxy signal at 3.01 ppm was still present.

Example 3 (EX-3)

Example 3 was made according to the procedure used for Comparative Example 1, except that the amounts of materials were as indicated for EX-3 in Table 2, including the 0.35 pbw of KAEBP Gel content measurements were performed on each of CE-1, CE-2, and EX-2, with gel wt. % results as summarized in Table 3.

TABLE 3

| Sample | Gel wt. % |
| --- | --- |
| CE-1 | 3.00 |
| CE-2 | 91.50 |
| EX-2 | 7.50 |

Approximately 50 grams of each polymer (CE-1, CE-2, EX-2) was individually hotmelt-blended in a Brabender at 160° C. at 100 rpm for 10 minutes.

Samples of EX-2 before and after hotmelt-blending were analyzed by proton NMR. The spectrum show the loss the of the ketal methoxy peak at 3.01 ppm in the hotmelt-blended polymer. The gel weight percent value of the EX-2 material after hotmelt-blending was found to be 80 wt. %.

A sample of EX-2 after hotmelt-blending was cured at 23 mJ UVC (and 200 mJ of UVB and 600 mJ of UVA) radiation using a UV fusion lamp, and the sample was analyzed for tan delta value, along with samples of CE-1, CE-2, and EX-2 material before hotmelt-blending, as described below.

Samples of CE-1, CE-2, EX-2 material before hotmelt-blending, and EX-2 material after hotmelt-blending and UV cure were pressed into 1.5 mm films for rheometric analysis. The samples were tested in a DHR2—stress controlled rheometer (TA Instruments) with environmental chamber attachment for heating and cooling the samples. A temperature ramp experiment was conducted on samples in between a 25 mm plate from 20° C. to 125° C. at 1 rad/sec oscillation frequency and at 3° C./minute ramp rate. The rheometer recorded the oscillation torque as a function of the angular displacement and processed the data to provide the storage and loss modulus, and thereby the tan delta of the samples. The resulting tan delta values were as summarized in Table 4.

TABLE 4

| Sample | UV cured | Tan delta at 125° C. |
| --- | --- | --- |
| CE-1 | No | 2.2 |
| CE-2 | No | 0.3 |
| EX-2 before hotmelt-blending | No | 1.5 |
| EX-2 after hotmelt-blending and UV cure | Yes | 0.2 |

Performance of EX-3 with and without an added tackifier was examined. For Examples 4 and 5 (EX-4 and EX-5), a sample of EX-3 was compounded in an extruder at 160° C. with an amount of a tackifier (FORAL 3085) indicated in Table 5. The resulting hotmelt was coated onto liners using a drop die on a twin screw extruder. The extrusion temperatures for the die and extruder were kept at 160° C. The extruded samples were coated at 3 mil (~76 micrometers) thickness. The samples were later laminated onto Mitsubishi 3SAB PET film and cured at 23 mJ UVC (and 200 mJ of UVB and 600 mJ of UVA) radiation using a UV fusion lamp. Adhesion properties of the resulting tapes were as summarized in Table 5.

TABLE 5

| Sample | Base polymer | FORAL 3085, pbw | Water, pbw | Coating thickness, mil (micrometers) | 180° peel force on SS, N/dm | Shear at 70° C., min |
| --- | --- | --- | --- | --- | --- | --- |
| EX-4 | EX-3 (100 pbw) | 0 | 0 | 3 (~76) | 32.4 | >10000 |
| EX-5 |  | 60 | 0 | 3 (~76) | 67.0 | >10000 |
| EX-6 |  | 0 | 0.33 | 3 (~76) | 28.1 | >10000 |
| EX-7 |  | 60 | 0.33 | 3 (~76) | 61.6 | >10000 |

For Examples 6 and 7 (EX-6 and EX-7), the processing was as for EX-4 and EX-5, except that water was added prior to the initial compounding step, in the amounts shown in Table 5. Adhesion properties of the resulting tapes were as summarized in Table 5.

In an alternate synthesis of a pre-adhesive composition, IOA (47.5 grams) was mixed with AA (2.5 grams), and to this mixture was added IRG651 (0.1 pbw), IOTG (0.04 pbw), and KAEBP (EX-1 crude material, 0.5 pbw). The mixture was transferred to a clear glass jar and purged with nitrogen gas for 60 seconds. The jar was then sealed and exposed to 350 nm centered blacklights and agitated. An exothermic reaction occurred and the material viscosity increased, forming a reaction syrup. The reaction mixture was determined to be approximately 35 wt. % converted (in terms of the reaction of acrylate monomer to form polymer), based on a percent solids test and NMR analysis.

To an aliquot of 38.2 grams of the reaction syrup in a reactor was then added thermal initiators and IOTG (0.016 pbw) as a solution in ethyl acetate (~0.9 pbw; the combinations of thermal initiators followed the general teachings outlined in the Examples of U.S. Pat. No. 7,968,661). The reactor was sealed and purged of oxygen, and then held under a positive nitrogen pressure. The reaction mixture was heated to 62° C., and the reaction proceeded adiabatically, to produce a pre-adhesive composition. The pre-adhesive composition had an intrinsic viscosity value of ~0.57, a monomer conversion to polymer of ~95 wt. %, and removal of the ketal protecting group was complete according to NMR analysis.

What is claimed is:

1. A protected photocrosslinker of the formula:

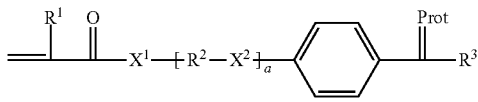

wherein
$R^1$ is H or $CH_3$;
each of $X^1$ and $X^2$ is —O— or —$NR^1$—;
$R^2$ is a divalent (hetero)hydrocarbyl group;
subscript a is 0 or 1;
Prot is a carbonyl protecting group;
$R^3$ is selected from:

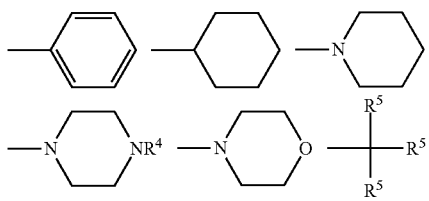

wherein each $R^4$ is H or a $C_1$ to $C_6$ alkyl group, $R^5$ is independently a hydroxyl group, a phenyl group, a $C_1$ to $C_6$ alkyl group, or a $C_1$ to $C_6$ alkoxy group.

2. The protected photocrosslinker of claim 1 wherein Prot is a cyclic or acyclic ketal, dithioketals, O-substituted cyanohydrins, substituted hydrazones, oxazolidines, imidazolidines and thiazolidines protecting groups.

3. The protected photocrosslinker of claim 1 where $X^1$—$R^2$—$X^2$ is —NH—$C(CH_3)_2$—CO—O—$(R^{10}$—$O)_b$—, where $R^{10}$ is a linear or branched alkylene, and subscript b is 0 or 1.

4. A polymerizable composition comprising a monomer mixture of at least one (meth)acrylate monomer, a photoinitiator and a protected photocrosslinker of claim 1.

5. The polymerizable composition of claim 4 wherein the monomer mixture comprises:
   a) 50-99 parts by weight of (meth)acrylate ester monomers;
   b) 1-50 parts by weight of polar monomers, inclusive of acid-functional monomers;
   wherein the sum of the monomers is 100 parts by weight.

6. The polymerizable composition of claim 5 wherein the monomer mixture comprises:
   a) 50-99.9 parts by weight of (meth)acrylate ester monomers;
   b) 0.1-15 parts by weight of acid-functional monomers;
   c) 0 to <50 parts by weight of polar monomers, exclusive of acid-functional monomers,
   wherein the sum of the monomers is 100 parts by weight.

7. The polymerizable composition of claim 4 comprising:
   a) 0.01 to 1.0 parts by weight of a photoinitiator, and
   b) 0.05 to 0.5 parts be weight of a protected photocrosslinker of claim 1,
   relative to 100 parts by weight of the monomer mixture.

8. A method of preparing a (meth)acrylate (co)polymer comprising the steps of:
   a) photopolymerizing a monomer mixture of at least one (meth)acrylate monomer, a photoinitiator and a protected photoinitiator of claim 4;
   b) deprotecting the protected photocrosslinker, and
   c) photocrosslinking the resulting copolymer.

9. The method of claim 8 wherein the monomer mixture of step a) comprises:
   50-99 parts by weight of (meth)acrylate ester monomers;
   1-50 parts by weight of polar monomers, inclusive of acid-functional monomers;
   wherein the sum of the monomers is 100 parts by weight.

10. The method of claim 8 wherein the monomer mixture of step a) comprises:
    50-99.9 parts by weight of (meth)acrylate ester monomers;
    0.1-15 parts by weight of acid-functional monomers;
    0 to <50 parts by weight of polar monomers, exclusive of acid-functional monomers,
    wherein the sum of the monomers is 100 parts by weight.

11. The method of claim 8 wherein the monomer mixture of the first photopolymerization step is fully converted to uncrosslinked copolymer.

12. The method of claim 8 wherein the monomer mixture of the first photopolymerization step is converted up to 30% to uncrosslinked copolymer.

13. The method of claim 8 wherein the product of step a) is a (meth)acrylate copolymer having pendent, protected photocrosslinker groups.

14. The method of claim 13 wherein the uncrosslinked copolymer is of the formula:

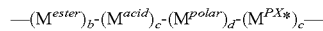

where
$M^{ester}$ represents polymerized monomer units derived from (meth)acrylate monomers,
$M^{acid}$ represents polymerized monomer units derived from acid functional monomers,
$M^{polar}$ represents polymerized monomer units derived from non-acid functional polar monomers,
$M^{PX*}$ represents polymerized monomer units derived from the protected photocrosslinker, and
subscripts b, c, d and e represent the parts by weight of each monomer in the copolymer.

15. The method of claim 8 wherein the step of deprotecting provides an uncrosslinked copolymer of the formula:

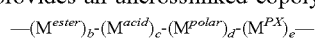

$M^{ester}$ represents polymerized monomer units derived from (meth)acrylate monomers,
$M^{acid}$ represents polymerized monomer units derived from acid functional monomers,
$M^{polar}$ represents polymerized monomer units derived from non-acid functional polar monomers,
$M^{PX}$ represents polymerized monomer units derived from the deprotected photocrosslinker, and
subscripts b, c, d and e represent the parts by weight of each monomer in the copolymer.

16. The method of claim 8 wherein the step of further photocrosslinking photolyzes the deprotected photocrosslinker group and crosslinks the (meth)acrylate polymer.

17. The method of claim 8 comprising the steps of:
   1) photopolymerizing a monomer mixture to provide a syrup polymer composition comprising a solute copolymer having pendent, protected photocrosslinking groups;
   2) thermally polymerizing the syrup polymer composition to produce a copolymer composition wherein the photocrosslinking groups are deprotected;
   3) optionally coating the copolymer composition of step 2), and
   4) photocrosslinking the copolymer composition by exposure to UV radiation.

18. A copolymer of the formula:

$$-(M^{ester})_b-(M^{acid})_c-(M^{polar})_d-(M^{PX*})_e-$$

where $M^{ester}$ represents polymerized monomer units derived from (meth)acrylate monomers, $M^{acid}$ represents polymerized monomer units derived from acid functional monomers, $M^{polar}$ represents polymerized monomer units derived from non-acid functional polar monomers, $M^{PX*}$ represents polymerized monomer units derived from the protected photocrosslinker of claim 4, and subscripts b, c, d and e represent the parts by weight of each monomer in the copolymer.

19. The copolymer of claim 18 comprising:
a) 50-99.9 parts by weight of (meth)acrylate ester monomers;
b) 0.1-15 parts by weight of acid-functional monomers;
c) 0 to <50 parts by weight of polar monomers, exclusive of acid-functional monomers, and
d) 0.05 to 0.5 parts be weight of the protected photocrosslinker;
relative to 100 parts by weight of the monomer mixture.

* * * * *

UNITED STATES PATENT AND TRADEMARK OFFICE
CERTIFICATE OF CORRECTION

PATENT NO. : 10,189,771 B2
APPLICATION NO. : 15/550830
DATED : January 29, 2019
INVENTOR(S) : Karl Benson It is certified that error appears in the above-identified patent and that said Letters Patent is hereby corrected as shown below:

In the Specification

Column 2,
Line 10, delete "gellation" and insert -- gelation --, therefor.
Line 45, delete "monvalent" and insert -- monovalent --, therefor.

Column 3,
Line 1, delete "benzthiazolyl." and insert -- benzothiazolyl. --, therefor.
Line 21, delete "supr" and insert -- supra. --, therefor.

Column 8,
Line 29, delete "anthraqinone," and insert -- anthraquinone, --, therefor.
Line 29, delete "anthraqinone," and insert -- anthraquinone, --, therefor.

Column 12,
Lines 16-18, delete " $-(M^{ester})_b-(M^{acid})_c-(M^{polar})_d-(M^{PX*})_e- \rightarrow -(M^{ester})_b-(M^{acid})_c-(M^{polar})_d-(M^{PX})_e-$ " and insert -- $-(M^{ester})_b-(M^{acid})_c-(M^{polar})_d-(M^{PX*})_e- \rightarrow -(M^{ester})_b-(M^{acid})_c-(M^{polar})_d-(M^{PX})_e-$ --, therefor.
Line 23, delete "monomers" and insert -- monomers, --, therefor.

Column 13,
Line 39, delete "peroxide," and insert -- peroxide. --, therefor.

Column 18,
Line 2, delete "pentaertythritol" and insert -- pentaerythritol --, therefor.
Line 24, delete "dicyclopenetadiene," and insert -- dicyclopentadiene, --, therefor
Line 45, delete "EASTOTACK." and insert -- EASTOTAC. --, therefor.

Signed and Sealed this
Ninth Day of April, 2019

Andrei Iancu
*Director of the United States Patent and Trademark Office*

Line 48, delete "KRISTLEX," and insert -- KRISTALEX, --, therefor.
Line 51, delete "NOVAREZ," and insert -- NOVARES, --, therefor.
Line 53, delete "HIKOTAC." and insert -- HIKOTACK. --, therefor.

Columns 21 & 22, Table 1,
Line 5, delete "thioglycoate" and insert -- thioglycolate --, therefor.

Column 21,
Line 51, delete "rotory evaporater." and insert -- rotary evaporator. --, therefor.
Line 62, delete "ajar," and insert -- a jar, --, therefor.

Column 23,
Line 6, after "KAEBP" insert -- . --.
Line 34, delete "the of" and insert -- of --, therefor.

In the Claims

Column 25,
Line 50, in Claim 6, delete "claim 5" and insert -- claim 4 --, therefor.
Line 67, in Claim 8, delete "claim 4;" and insert -- claim 1; --, therefor.

Column 26,
Line 27, in Claim 14, delete " $—(M^{ester})_b\text{-}(M^{acid})_c\text{-}(M^{polar})_d\text{-}(M^{PX*})_c—$ "
and insert -- $\text{-}(M^{ester})_b\text{-}(M^{acid})_c\text{-}(M^{polar})_d\text{-}(M^{PX*})_e\text{-}$ --, therefor.

Column 27,
Line 12, in Claim 18, delete "claim 4," and insert -- claim 1, --, therefor.